United States Patent [19]

Ferrara

[11] Patent Number: 4,995,872
[45] Date of Patent: Feb. 26, 1991

[54] EXPANDABLE CATHETER AND BRIDGE DEVICE

[76] Inventor: Janice J. Ferrara, 11605 Timberly Waye, Richmond, Va. 23233

[21] Appl. No.: 416,983

[22] Filed: Oct. 4, 1989

[51] Int. Cl.⁵ .......................................... A61M 25/00
[52] U.S. Cl. .................................. 604/280; 604/283; 604/264; 604/93
[58] Field of Search ............... 604/280, 283, 284, 264, 604/93, 95

[56] References Cited

U.S. PATENT DOCUMENTS

| | | |
|---|---|---|
| 2,009,825 | 7/1935 | Wappler . |
| 3,606,889 | 9/1971 | Arblaster . |
| 3,886,933 | 6/1975 | Mori ......................................... 128/7 |
| 3,894,540 | 7/1975 | Bonner, Jr. . |
| 4,062,363 | 12/1977 | Bonner, Jr. . |
| 4,168,699 | 9/1979 | Hauser ................................ 128/768 |
| 4,327,735 | 5/1982 | Hampson . |
| 4,568,334 | 2/1986 | Lynn .................................... 604/171 |
| 4,569,347 | 2/1986 | Frisbie . |
| 4,593,690 | 6/1986 | Sheridan et al. ...................... 604/283 |
| 4,620,848 | 11/1986 | Sutherland et al. ................. 604/154 |

Primary Examiner—Stephen C. Pellegrino
Attorney, Agent, or Firm—Griffin Branigan & Butler

[57] ABSTRACT

An expandable catheter and bridge device for use in endoscopic/cystoscopic procedures utilizing a laterally flexible tubular catheter includes a longitudinally expandable section, and further comprising a rigid bridge-like handle structure to facilitate catheter maneuvering and deployment manipulation. The catheter tube is insertible through a passage of an endoscopic instrument while the catheter's expandable section is expanded in length through the coaction of manually applied tension and the expanding means disposed in one of the catheter-encircling ends of the bridge-like handle structure as the catheter is drawn therethrough. At the other catheter-encircling end, the bridge-like handle structure is secured to a passage entry of the endoscopic instrument. The bridge-like handle structure is provided with a snap-in cradle fitting to securely hold a syringe which can be connected to the end of the catheter tube.

37 Claims, 7 Drawing Sheets

EXPANDABLE CATHETER AND BRIDGE DEVICE

BACKGROUND OF THE INVENTION

1. Field of the Invention

This invention relates to catheters, for instance for use in cystoscopy and in ureteroscopy, and more particularly to ureteral and urethral catheter devices which can be inserted into a part of a patient through endoscopic instruments for various catheterization purposes, for example during cystoscopic and ureteroscopic procedures.

2. Prior Art And Other Considerations

In general, catheterization procedures utilize endoscopes, cystoscopes, or ureteroscopes provided with at least one passage for insertion of a catheter therethrough. These endoscopic instruments may be of a rigid or flexible type and comprise optical paths for illuminating and viewing of target regions. The passage for insertion of a catheter is provided with an entry in a so-called endoscope bridge arrangement often having coupling and sealing means disposed in this entry. Generally, a catheter is inserted by manipulative threading of the catheter into the entry and through the catheter passage of the particular endoscopic instrument to the target area. Delicate manipulative maneuvering and guidance is required to safely and accurately extend and position the catheter tip to the required target area, for instance to a ureteral orifice and into a ureter. Customarily, catheters for such purposes comprise a laterally flexible, but inextensible tubular structure, often having a tip shaped to suit various purposes.

A difficulty associated with the threading and manipulative maneuvering of conventional catheters through endoscopic instruments to particular target regions is caused by the need to simultaneously hold and guide the endoscopic instrument, to view the region through an ocular, to perform various adjustments and to operate endoscope controls, as well as to handle the catheter and attachments associated therewith. Moreover, spillage of bodily fluids is often rather difficult to avoid with conventional catheter arrangements. Not only is considerable skill required, but the procedure sorely taxes the manipulative capability of the urologist's hands to perform a plurality of control tasks more or less simultaneously. Additionally, the length of ureteral catheters, commonly about twenty six inches and longer, provides for cumbersome storage and handling in deployment, particularly due to the need for maintaining the catheter under aseptic conditions.

Catheters of various kinds have been in use for about a century and, in combination with endoscopes, are now routinely employed, particularly also in urological diagnostic procedures. Catheters which originally used slender tubes of metal have evolved into tubes of rubber and plastic in a great variety of shapes and sizes adapted to different specialty tasks.

For instance, U.S. Pat. No. 2,009,825 issued to Wappler discloses an aseptic catheter-handling device relating particularly to the sterile manipulation of catheters. Wappler shows a catheter-grasping member carried at the forward end of a flexible tube that accommodates the longitudinally movable catheter therein and that is adapted to releasably engage the forwardly projecting portion of the catheter.

Another catheter device disclosed by Bonner, Jr., in U.S. Pat. No. 3,894,540 comprises an elongated flexible conduit including a protective sheath in form of telescoping tubing or in accordion-pleated tubular form.

Arblaster discloses in U.S. Pat. No. 3,606,889 a guard accessory for catheters which includes a tubular housing provided with shallow corrugations to facilitate axial expansion and contraction.

Mori et al discloses in U.S. Pat. No. 3,886,933 a ureteral catheter device insertable through a cystoscope.

U.S. Pat. No. 4,568,334 issued to Lynn discloses an intravascular catheter container assembly including a pleated glove which surrounds a portion of the catheter. U.S. Pat. No. s 4,062,363 issued to Bonner and U.S. Pat. No. 4,327,735 issued to Hampson also show pleated catheter guards.

Frisbie discloses in U.S. Pat. No. 4,569,347 a catheter-introducing device having a Luer fitting, and Hauser discloses in U.S. Pat. No. 4,168,699 a catheter having an inner tube with a loop used to hold the tube in a retracted position.

The expandable catheter and bridge device of the present invention is intended to overcome the difficulties of the prior art, particularly in respect to improving ease of handleability during endoscopic procedures, to reduce occurrences of spillage of body fluids, and to significantly reduce pre-packaged catheter lengths and free lengths to be manipulated during deployment.

Accordingly, an overall feature of the invention is the provision of a catheter device comprising a laterally flexible tubular structure including a longitudinally expandable section. A further feature includes a rigid bridge-like handle structure for attachment to an endoscope, to facilitate expanding the expandable section, and to facilitate catheter maneuvering and manipulation during endoscopic procedures while reducing incidence of fluid spillage. The structure also permits significantly reduced pre-packaged catheter lengths and free catheter lengths to be aseptically manipulated and deployed in use.

SUMMARY OF THE INVENTION

In accordance with principles of the present invention, an expandable catheter and bridge device comprises a laterally flexible tubular catheter structure including a longitudinally expandable section. The device further comprises a rigid bridge-like structure each of whose two ends encircle the catheter in longitudinally-spaced locations thereof, whereby the catheter can be slidably axially moved and simultaneously longitudinally expanded by appropriate manipulation through the encircling bridge ends so that the catheter is guided thereby. One encircling bridge end is attachable to a passage entry port of an endoscope. The other encircling bridge end is adapted internally to facilitate longitudinal expansion of the catheter's expandable section during manipulation, deployment, and insertion of the catheter through the passage in the endoscope.

The catheter tube, per se, has a proximal end for insertion into a patient's body part and a distal end that can be adapted for connection to a closure plug or to further instruments. The proximal end can be provided with an appropriately-shaped tip. A snap-in cradle fitting is provided upon the bridge-like handle structure to securely hold and facilitate use of such further instruments such as syringes which may be connected to the distal end of the catheter tube.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout different views. The drawings are schematic and not necessarily to scale, emphasis instead being placed upon illustrating principles of the invention.

DESCRIPTION OF THE PREFERRED EMBODIMENTS

Figure 1:
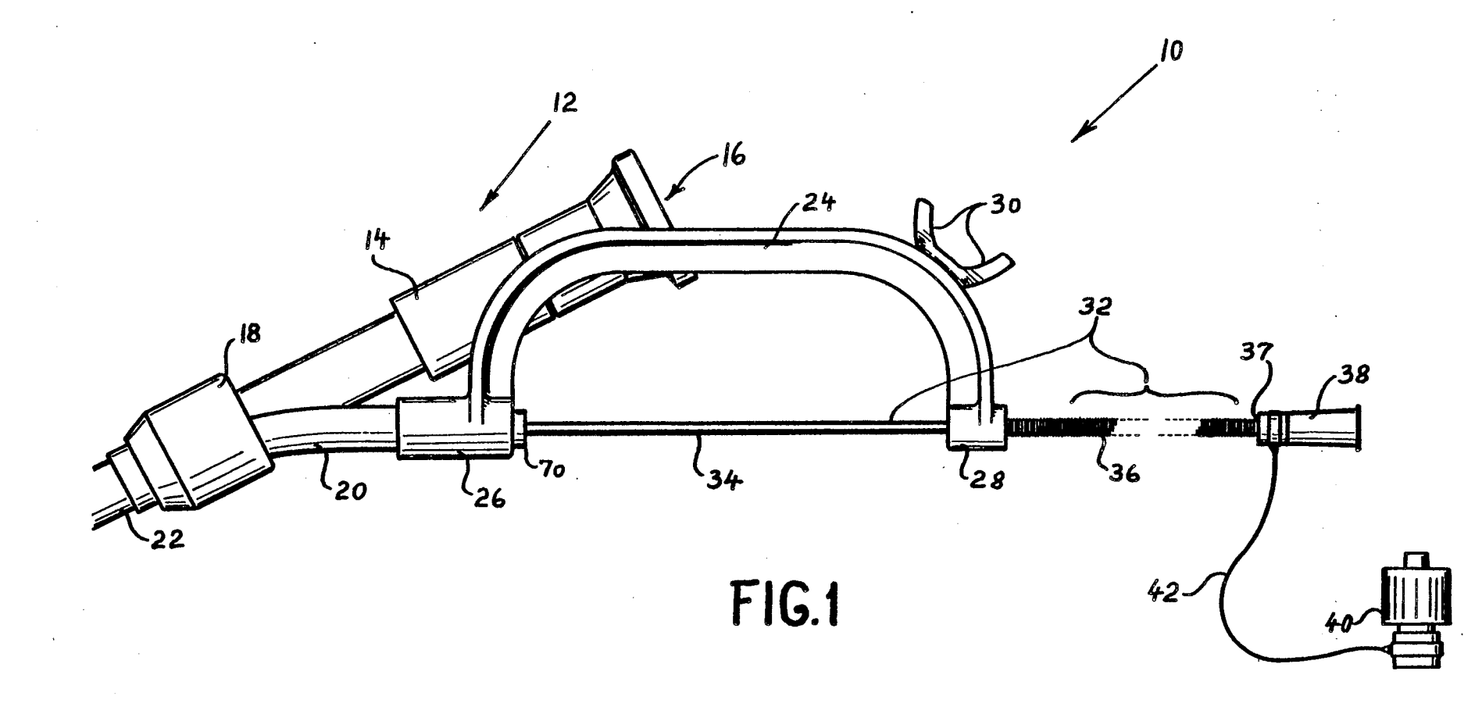
FIG. 1 is a schematic side view of an embodiment, according to the present invention, of an expandable catheter and bridge device secured to an endoscope (such as a cystoscope) for use in combination therewith, the endoscope being schematically partially depicted.

Referring now to FIG. 1, an expandable catheter and bridge device 10 is shown secured to a cystoscope 12 (or a ureteroscope or other endoscopic instrument). Cystoscope 12 has optics comprised in a main structure 14 and an ocular 16 disposed at a distal end thereof. Further comprised in cystoscope 12 is a joint 18 to which leads a passage entry housing 20. Main structure 14 continues as cystoscope sheath 22 that includes along its length the optics for viewing and illuminating and at least one passage for the introduction therethrough of various devices such as, for instance, catheters. The portion of cystoscope 12 that includes joint 18 and passage entry housing 20 is commonly called a cystoscope bridge. Cystoscope sheath 22 can be rigid or flexible and usually is further reduced in diameter along its length (not shown here) to facilitate introduction into bodily passages, for instance into the urethra.

A bridge means 24 (of a catheter and bridge device 10) is provided with proximal and distal catheter-encircling ends 26 and 28, respectively. Proximal catheter-encircling end 26 is provided with attachment means for being sealedly attached and secured to passage entry housing 20. A cradle 30 is disposed upon bridge means 24 for optional snap-in retention of a syringe. Proximal and distal catheter-encircling ends 26 and 28 are each provided with a through-opening, the through-openings being substantially in-line and having catheter means 32 threaded therethrough.

Catheter means 32 comprises a longitudinally inextensible section 34 and a longitudinally expandable section 36. Shown attached to the distal end 37 of 25 expandable section 36 is a connection adaptor 38 being provided with a mating closure cap 40 that is flexibly and captively attached via a tie 42. As depicted, the connection adaptor 38 is a conventional "Luer" type female adaptor, and closure cap 40 is of the same but mating kind. This end of the catheter means 32 is securely and sealedly capped and closed off when closure cap 40 is connected to connection adaptor 38. Connection adaptor 38 can be used to optionally connect to various instruments, for instance syringes, drainage or Foley bags, extension tubes, etc.

Figure 2:
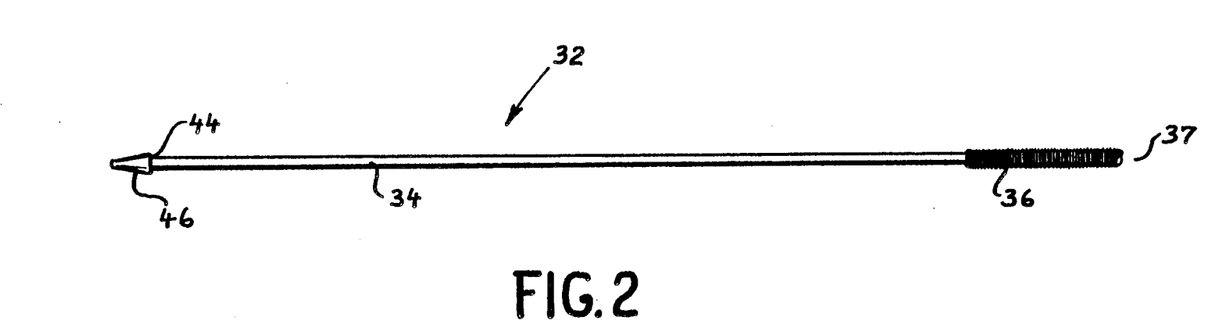
FIG. 2 is a schematic side view of an expandable catheter means embodiment of the invention.

Referring to FIG. 2, catheter means 32 comprises longitudinally inextensible section 34 having a proximal end 44 and longitudinally expandable section 36 having distal end 37. A tip 46 is connected to proximal end 44. Tip 46 is of a conical shape, however a variety of different tip shapes and sizes can be used for various procedures in accordance with customary practice. Prior to employment of catheter means 32 in a combination as shown in FIG. 1, the components are assembled so that proximal end 44 is inserted for a length of approximately two inches into passage entry housing 20.

Figure 2A:
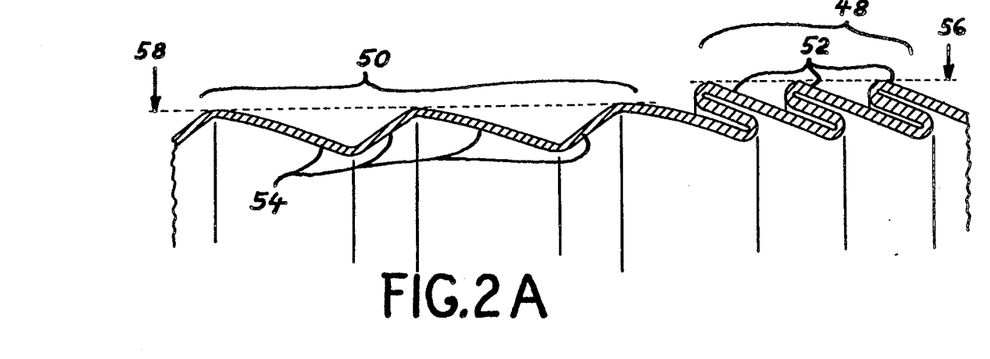
FIG. 2A is a schematic fragmented axial section view of an embodiment of a longitudinally expandable portion of a catheter device of the invention.

Referring now to FIG. 2A, a wall portion of an embodiment of longitudinally expandable section 36 of catheter means 32 is shown by an unexpanded portion 48 and a substantially expanded portion 50. Unexpanded corrugations 52 of unexpanded portion 48 are folded over in overlapping manner in a preferred embodiment shown here. When expandable section 36 is longitudinally tensioned beyond a threshold force, unexpanded corrugations 52 unfold in a snap-actional manner to a form generally as shown by expanded corrugations 54. As indicated by dashed lines, the outside diameter 56 of unexpanded portion 48 is thereby reduced to the outside diameter of the expanded portion 58. Adjacent corrugation sides are of unequal length, as shown. 25 It will be appreciated that expanded portion 50 has attained a substantial resistance and strength against longitudinal compression strain. The mentioned snap-actional manner by which unexpanded corrugations 52 unfold into expanded corrugation 54 can be likened to the manner by which bistable Belleville washers known in the engineering arts can be forced to snap between their two stable states, namely having the convex face snap over to become concave. The shown structure of unexpanded and expanded corrugations is generally similar to the structure of various types of commercially available plastic soda straws having a flexible and expandable portion often provided with similarly overlapped and folded over corrugations.

Figure 2B:
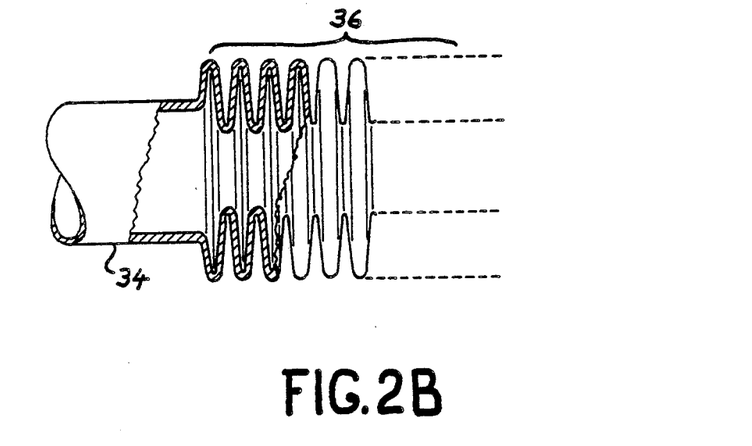
FIG. 2B is a schematic fragmented side view and partial axial section of a catheter device of the invention showing an inextensible portion adjoining an expandable portion thereof.

Referring to FIG. 2B (adjacent FIG. 8), another embodiment of longitudinally expandable section 36 is shown here (together with longitudinally inextensible section 34), wherein corrugation sides are of substantially equal lengths in the manner of accordion or bellows folds. In order to attain substantial resistance and strength against longitudinal compression-strain subsequent to expansion, the longitudinal expansion of section 36 occurs substantially by deformation of the folds which hardens the material in the fold regions to further provide such strength. Appropriate material selections provide for such characteristics.

In view of the foregoing descriptions, it will be apparent that circular corrugations in expandable section 36 of catheter means 32 are preferred. However, other than the specifically described corrugation shapes can be used instead; for example, different fold shapes and orientations and, for instance, helical corrugations.

Figure 3:
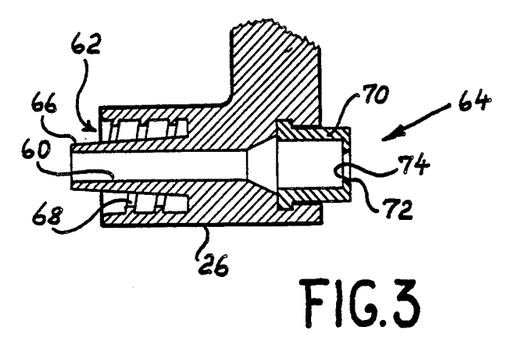
FIG. 3 is a schematic axial section view of a proximal catheter-encircling end embodiment of the bridge means included in the depictions of FIGS. 1 and 9.

Referring now to FIG. 3, proximal catheter-encircling end 26 (of FIG. 1) comprises guiding means 60 for guiding the catheter means 32 through, attachment means 62 for sealedly securing catheter-encircling end 26 to passage 25 entry housings of endoscopes, such as passage entry housing 20 of cystoscope 12. Sealing means 64 slidably seals guiding means 60 against the outside surface of a catheter means 32.

Guiding means 60 comprises a clearance hole through proximal catheter-encircling end 26 which may be variously shaped to slidably guide catheter means threaded therethrough. Attachment means 62, as shown here, is substantially in form of a conventional male "Luer" type fitting which provides for sealing along a conical taper 66 and for securing by screw threads 68 in conjunction with a correspondingly mating female "Luer" adaptor fitting that is disposed at the end of the passage entry housing of a suitable endoscope, for instance at passage entry housing 20 of cystoscope 12. Alternately, different conventional fitting adaptations can be employed instead, provided that the indicated sealing and securing is achieved by attachment means 62. Proximal catheter-encircling end 26, for instance, can have the outside portion of its proximal end that includes attachment means 62 and screw threads 68, formed as a floating nut that is captively retained by a ridge formed in the periphery of the shank for the conical taper 66 in the manner of certain conventional "Luer" lock fittings. Bridge means 24 can then be oriented at any desired angle with respect to cystoscope 12 when attached thereto.

Sealing means 64 is shown in form of a soft rubber or other elastomeric cap 70, being sealedly retained within proximal catheter-encircling end 26, and having a sealing orifice 72. Sealing orifice 72 is preferably shaped to have a smaller diameter 74 on the inner side and a larger diameter on the outer side, wherein at least inner diameter 74 interferes with the outer diameter of catheter means 32 (inextensible section 34 and expanded expandable section 36) 25 to provide for slidable sealing therebetween. Sealing means 64 has the advantageous characteristic in that it is replaceable by pulling it out of its retaining groove and by snapping in a replacement. This is particularly advantageous for adaptation purposes to different diameter catheter means 32.

Figure 4:
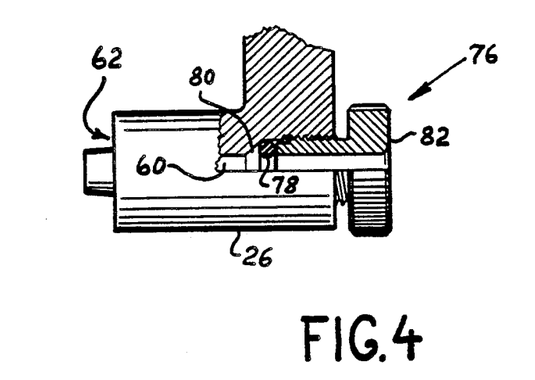
FIG. 4 is a schematic partial axial section view of an alternate proximal catheter-encircling end embodiment of the bridge means included in the depictions in FIGS. 1 and 9.

Referring now to FIG. 4, another sealing means embodiment is shown as an example of an alternate to sealing means 64 (of FIG. 3) in the form of an adjustable gland 76. Adjustable gland 76 is substantially of a conventional structure, comprising an 'o' ring or similar soft elastomeric ring-like structure seal 78 that is retained concentrically with guiding means 60 in a tapered bore 80. A compression screw 82, that is provided with an axial clearance bore for catheter means 32, is threadedly disposed concentrically with guiding means 60 and compresses seal 78 into tapered bore 80 when screwed in, so that seal 78 is deformed thereby to decrease its inner diameter to seal onto the outer diameter of catheter means 32 (when present in guiding means 60). Screw adjustment of compression screw 82 provides for adjustability of slidable sealing between seal 78 and catheter means 32 and further provides an optional adjustable clamping facility for secure clamping and restraining of catheter means 32 in any desired axial relationship. Compression screw 82 is provided with a knurled head for easy manual adjustment. Adjustable gland 76 has also the advantageous characteristic in that its 'o' ring is exchangeable to facilitate seal size adaptation to different diameter catheter means 32.

It should be understood that alternate sealing structures can be used instead of sealing means 64 or adjustable gland 76 shown in FIGS. 3 and 4, respectively. Moreover, in situations not necessarily requiring such sealing, sealing means can be omitted.

Figure 5:
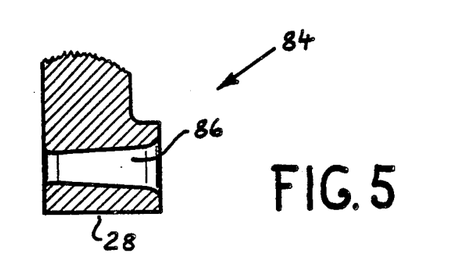
FIG. 5 is a schematic axial section view of a distal catheter-encircling end embodiment of the bridge means included in the depictions of FIGS. 1 and 9.

FIG. 5 shows an embodiment of an expanding means 84 included in distal catheter-encircling end 28. Expanding means 84 is provided in a general form of a tapered bore 86 whose diameter reduces in the direction in which catheter means 32 is drawn therethrough for expansion of expandable section 36 thereof. Both ends of the bore are preferably chamfered or radiused. The larger diameter of tapered bore 86 is equal to or slightly larger than the diameter of the unexpanded portion of expandable section 36 and the smallest diameter is equal to o slightly larger than the expanded portion of expandable section 36. It should be understood that the diameter of inextensible section 34 of catheter means 32 is approximately equal to the diameter of the expanded portion of expandable section 36, and can be slightly smaller or slightly larger, but must be smaller than the diameter of the unexpanded portion of expandable section 36. In this respect, tapered bore 86 serves to slidingly guide catheter means 32 therethrough, but particularly also serves for expanding of the corrugations of expandable section 36.

As catheter means 32 is drawn through tapered bore 86 (from right to left) outer diameter edges of the corrugations of expandable section 36 are radially forced inwardly and retarded by friction while their folds are axially pulled apart in snap-actional manner to flatten out and expand the corrugations.

Figure 6:
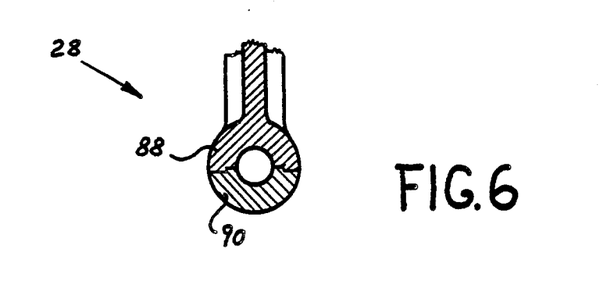
FIG. 6 is a schematic diametral section view of a distal catheter-encircling end embodiment of the bridge means included in the depictions in FIGS. 1 and 9.
Figure 7:
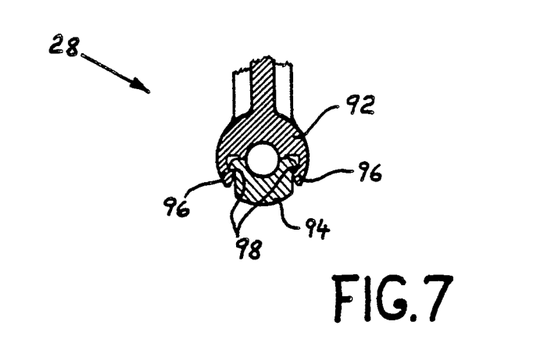
FIG. 7 is a schematic diametral section view of an alternate embodiment of the distal catheter-encircling end of the bridge means included in FIGS. 1 and 9.

FIGS. 6 and 7 depict different alternate embodiments of expanding means 84 comprised in distal catheter-encircling end 28 to facilitate assembly of certain catheter means 32 together with and within bridge means 24. As hereinbefore described, the catheter means is threaded through distal and proximal catheter-encircling ends 28 and 26, respectively, prior to use of the combined device. This assembly can be performed, for some combination versions, just prior to use, but for some combinations it was to be performed during manufacturing.

For instance, a catheter means comprising a tip 46 having a smaller outer diameter than the smallest opening diameter through the components of proximal and distal catheter-encircling ends 26 and 28 (or catheter means used without a tip 46) can be threaded therethrough at any time (proximal end 44 first). One should note that sealing orifice 72 in elastomeric cap 70 is elastically expandable and, therefore, does not represent a limiting smallest opening diameter. However, catheter means having larger diameter tips 46 are not thusly threadable. In this regard, it should be further noted, that the smallest diameter of guiding means 60 in proximal catheter-encircling end 26 allows clearance for most larger size tips 46 and at least also for the outer diameter of unexpanded expandable section 36.

Yet the smallest diameter opening within expanding means 84 is necessarily of a size between the diameters of the inextensible section 34 and the expandable section 36 of catheter means 32 and, therefore, does not permit threading therethrough of catheter means 32 having a tip 46 with a diameter substantially larger than that of inextensible section 34.

In order to provide assembly facilities to accommodate larger tips 46, threading of catheter means 32, distal end 37 first, is furnished by the following provisions.

As depicted in FIG. 6, distal catheter-encircling end 28 is split into two parts, namely upper and lower portions 88 and 90, respectively, having mutual alignment means in form of mating ridges provided in the mating region so that alignment of the bore sizes in expanding means 84 is achieved when the two halves are appropriately joined. Subsequent to laying in of catheter means 32, the two halves are joined, for example by adhesive bonding or by ultrasonic welding, which generally, but not necessarily, needs to be performed in manufacturing.

Depicted in FIG. 7 is an alternate embodiment of a distal catheter-encircling end 28 comprised of split portions, namely upper and lower parts 92 and 94, respectively. Mutual alignment means are here also provided to assure alignment particularly in the bore region when the two parts are appropriately joined. Subsequent to laying in of catheter means 32, the two parts 92 and 94 are joined by snap-fitting together. As indicated, opposed elastic barblike extensions 96 in upper part 92 snap over opposed mating barbs 98 in lower part 98, whereby a secure rigid assembly is achieved. This assembly can be performed during manufacturing, but can easily also be performed substantially manually just prior to use of the device.

By use of such provisions as shown in FIGS. 6 or 7, threading of catheter means 32 through distal catheter-encircling end 28 can be avoided (replaced by laying-in) and assembly of an expandable catheter and bridge device including larger tips 46 is facilitated. By example, distal end 37, prior to having connection adaptor 38 attached thereto, is threaded (from left to right) through proximal catheter-encircling end 26, and is layed into a split portion of distal catheter-encircling end 28 which is joined to the other split portion thereof, as hereinabove described.

Referring for the moment back to FIG. 1, in the immediately hereinabove described embodiments accommodating larger tips 46, attachment of connection adaptor 38 to distal end 37 of catheter means 32 can be performed in manufacturing subsequently to the hereinabove indicated assembly procedure, for instance by ultrasonic welding or adhesive bonding. Alternately, other manually attachable connection adaptors of conventional type can be attached at any time even immediately prior to use of the device or even during use thereof. Such manually attachable connection adaptors are commonly available and are usually of a compression fitting type, utilizing an 'o' ring that is compressed onto the catheter tube by a screw fitting (similar to the gland 76 shown in FIG. 4). These connection adaptors are also available with "Luer" type fittings, whereby the same facility can be obtained as is shown by connection adaptor 38 (in FIG. 1).

Figure 8:
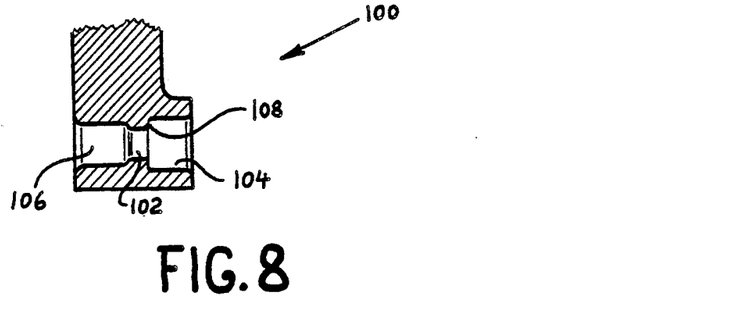
FIG. 8 is a schematic axial section view of an alternate embodiment of the distal catheter-encircling end of the bridge means included in FIGS. 1 and 9.

Referring now to FIG. 8, an alternate embodiment to expanding means 84 (shown in FIG. 5) is depicted therein as expanding means 100 included in distal catheter encircling end 28. Use of expanding means 100 is preferred in conjunction with the structure of expandable section 36 (of catheter means 32) shown in FIG. 2A. Expanding means 100 comprises concentric stepped bores including a smallest diameter hole 102, a counterbore 104 (from the right side), and a counterbore 106 (from the left side).

The transition between counterbore 104 and hole 102 is in form of a substantially diametral ledge 108 having an edge which is slightly chamfered or radiused to avoid cutting into or abrasion of the surface of catheter means 32 while it is drawn through expanding means 100 (from right to left). Outer edges of counterbores 104 and 106 are chamfered or radiused for similar purposes. Counterbore 104 serves to guide catheter means 32 toward hole 102 and, therefore has a diameter that is somewhat larger than the outside diameter of expandable section 36 in unexpanded form. Counterbore 104 can alternately be tapered toward hole 102 for this purpose. However, the smallest diameter of counterbore 104 near ledge 108 is at least equal to or larger than the diameter of unexpanded expandable section 36 so that no interference friction occurs therebetween. The diameter of hole 102 is at least equal to or slightly smaller or larger than the diameter of expandable section 36 in expanded form and specifically smaller than the diameter of unexpanded expandable section 36. Counterbore 106 is simply a relatively large clearance opening for passing through expanded expandable section 36 (and initially inextensible section 34) while guiding it to some extent.

As hereinbefore described in conjunction with FIGS. 6 and 7, Expanding means 100 can be constructed from split halves, in similar structures as hereinbefore described in conjunction with FIGS. 6 and 7, to facilitate assembly of the expandable catheter and bridge device, particularly in embodiments wherein catheter means 32 include large diameter tips 46.

In regard to the function of expanding means 100, particular reference is made also to FIGS. 1, 2, and 2A (in conjunction with FIG. 8) to describe by example the expansion of catheter means 32 during use. When properly assembled for use, catheter means 32 in its length portion of inextensible section 34 is disposed through counterbore 106 and farther at least through hole 102, continuing therebeyond (toward the right) with its length portion of expandable section 36. In use, as catheter means 32 is manually drawn through expanding means 100 (toward the left), unexpanded corrugations 52 of the unexpanded portion 48 of expandable section 36, one after another, bottom upon ledge 108 and are forced to unfold or expand into expanded corrugations 54 of expanded portion 50.

Figure 9:
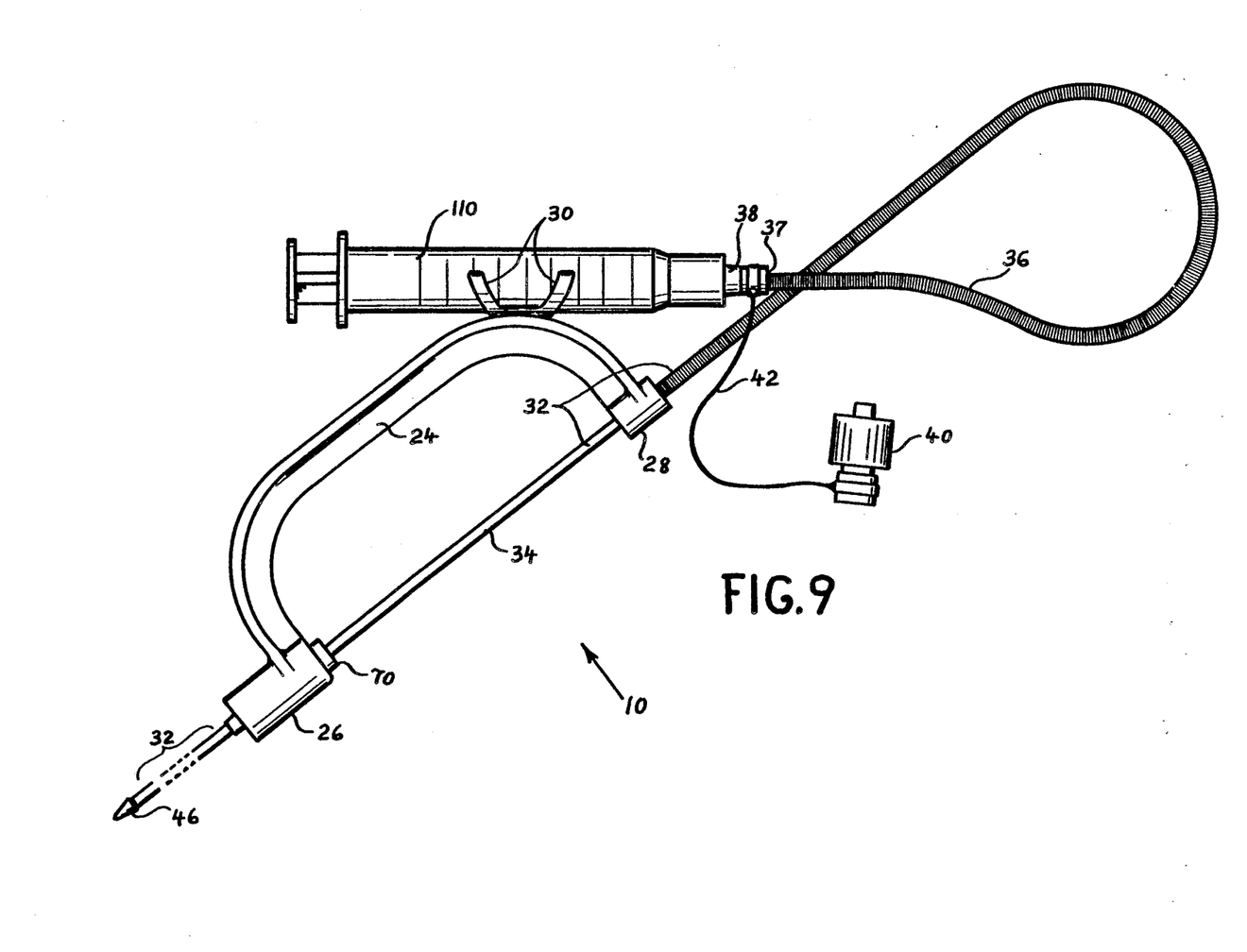
FIG. 9 is a schematic side view of an expandable catheter and bridge device, according to the present invention, including a syringe retained in a cradle of the bridge means and attached to the distal end of the catheter tube.

Referring now to FIG. 9, the expandable catheter and bridge device 10 of the present invention is shown here to particularly include a syringe 110 mounted and retained by snap-action in cradle 30. Syringe 110 is connected (for example by a male "Luer" lock) to connection adaptor 38 that is attached to distal end 37 of expandable section 36 of catheter means 32. With the further exception that FIG. 9 does not show cystoscope 12, the expandable catheter and bridge device 10 shown here is as depicted in FIG. 1.

In use during surgical procedures, the shown combination facilitates use of syringe 110 for introduction to and extraction of fluids through catheter means 32. Retention of syringe 110 upon bridge means 24 provides for easy one-handed operation of the syringe in a fixed and easy to access position, as opposed to customary conventional practice, whereby a syringe is only attached to the distal end of a generally loosely trailing catheter tube, While at times being temporarily and comparatively insecurely taped to a convenient available surface.

In use of the expandable catheter and bridge device of the present invention, the device is attached to an appropriate endoscope instrument, for example a ureteroscope (or cystoscope 12) as shown in FIG. 1. While viewing the target region through ocular 16, the urologist manipulates and draws with the fingers of one hand (between proximal and distal catheter-encircling ends 26 and 28) catheter means 32 through distal catheter-encircling end toward proximal catheter-encircling end. Catheter means 32 is thusly also pushed into and through the endoscope. As expandable section 36 of catheter means 32 is drawn through the expanding means in distal catheter-encircling end 28, expandable section 36 is longitudinally expanded, as hereinbefore described in detail.

As hereinbefore described in conjunction with FIG. 1 and also with FIGS. 3 and 4, proximal catheter-encircling end 26 is, in use, sealedly attached to passage entry housing 20 of cystoscope 12 (or of another endoscope). Whereas certain types of endoscopes are equipped with an entry to passage entry housing 20 that is suited to coupling with and attachment to a male "Luer" lock type configuration as for instance shown in FIG. 3 (conical taper 66, attachment means 62), certain other endoscopes do not provide entries that are suited for such coupling. However, most, if not all other endoscopes have an entry to passage entry housing 20 in the form of a metal tube provided with a substantially circular lip disposed about the outer periphery of an entry face. In order to provide the capability for sealedly attaching and securing the expandable catheter and bridge device, according to the present invention, also to endoscopes of the latter type, appropriate coupling adaptations are provided, as will be described in the following in conjunction with FIGS. 10, 11, 12, and 13.

Figure 10:
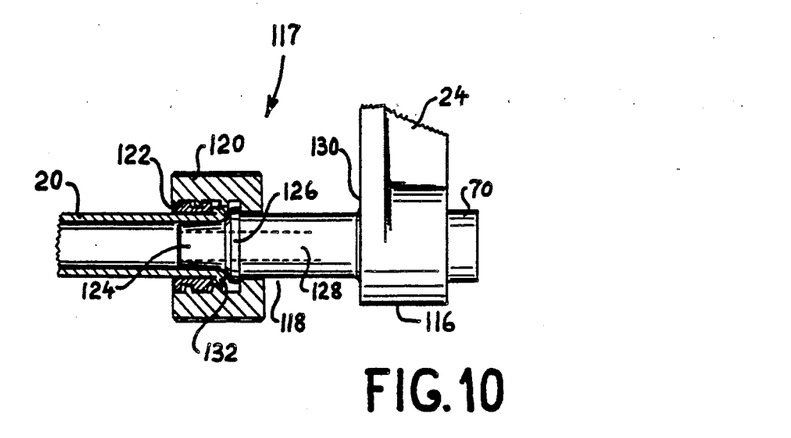
FIG. 10 is a schematic side view and partial section of a proximal catheter-encircling end embodiment of the bridge means included in the depictions of FIGS. 1 and 9, as attached to a sectioned fragment of a passage entry housing of an endoscope (such as a cystoscope)

Referring now particularly to FIG. 10, a proximal catheter-encircling end 116 is shown here whose internal structure and the structure disposed on the right side is substantially similar to the structure shown in FIG. 3, but whose proximal extension (toward the left) comprises coupler adaptation means 117 for sealedly attaching and securing proximal catheter-encircling end 116 to passage entry housing 20. Coupler adaptation means 117 comprises a tie tube 118, a coupler nut 120, and collar means 122. Tie tube 118 is a tubular extension of proximal catheter-encircling end 116 and is provided with a tapered end 124 and, disposed adjacently to the larger diameter thereof, a peripheral ridge 126. A shank portion 128, having a substantially constant outside diameter, extends between ridge 126 and proximal face 130 of proximal catheter-encircling end 116.

Coupler nut 120 encircles tie tube 118 and is freely axially slidable therealong and rotatable thereabout, yet it is captively retained by ridge 126 upon shank portion 128. Endoscope passage entry housing 20 (fragmentally shown here) is provided with a lip 132 disposed about its tubular entry opening. The outside diameter of passage entry housing 20 (at least over an axial distance corresponding to the axial length of collar means 122) adjacently to lip 132 is smaller than the outside diameter of lip 132. Collar means 122 encircles passage entry housing 20 adjacently to lip 132. Collar means 122 is provided with external screw threads mating with internal screw threads in coupler nut 120.

In assembly, as shown here in FIG. 10, tapered end 124 of tie tube 118 is inserted into passage entry housing 20 until it seals against the bore thereof. Coupler nut 120 is screwed onto collar means 122, whereby ridge 126 is forced toward lip 132 and proximal catheter-encircling end 116 is attached and sealedly secured to passage entry housing 20. Detachment of proximal catheter-encircling end 116 from passage entry housing 20 is performed by unscrewing of coupler nut 120 and withdrawing of tapered end 124.

Figure 12:
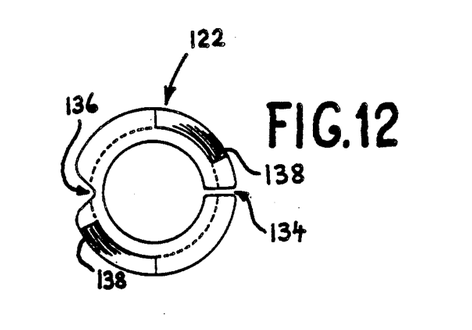
FIG. 12 is a schematic enlarged face elevational view of a coupler collar shown in FIG. 10.
Figure 13:
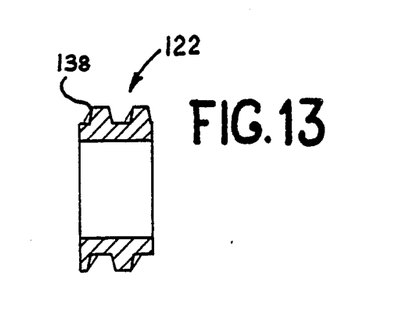
FIG. 13 is a schematic axial section view of the coupler collar shown in FIG. 12.

Referring now to FIGS. 12 and 13, collar means 122 shown therein has a ring-shaped body that is provided with a radial split 134 and a radially relatively thin hinge means 136 disposed diametrically oppositely thereto. The outside periphery of collar means 122 is provided with screw threads 138, for instance double start threads, as indicated here. Screw threads are preferably of the acme-thread or trapezoidal thread shape, although other thread types can be alternately used. Coupler nut 120 (FIG. 10) mates and engages with its threads screw threads 138.

Hinge means 136 in conjunction with split 134 are provided to permit mounting of collar means 122 about passage entry housing 20 behind ridge 126, since passage entry housing 20 is usually rigidly connected to an endoscope structure and, therefore, does not permit threading over of a closed ring structure of a collar. This can be visualized in view of FIG. 1, for instance. Hinge means 136 is preferably simply a thin material section that has substantial tensile strength, but is easily bent (along an axial direction) to a sufficiently open position for collar means 122 to be placed about passage entry housing 20 and again re-bent to encircle passage entry housing 20. Once screw threads 138 are engaged with the corresponding screw threads of coupler nut 120, collar means 122 tightly encircles passage entry housing 20 and is drawn by further tightening of coupler nut 120 against ridge 126. Friction between the surfaces of passage entry housing 20 and of ridge 126 with respect to the tightened collar means 122 does not allow relative rotation therebetween. In order to enhance such clamping friction, the bore of collar means 122 can be sized to a slightly smaller diameter than the outside diameter of passage entry housing 20 and, further, can be provided with axial ridges and/or with a film of pressure sensitive high friction material.

An alternate provision to ensure that collar means 122 does not revolve in relation to passage entry housing 20 while coupler nut 120 is threadedly tightened (or loosened) thereover can be a leftward extension of collar means 122 having a larger outer diameter for example grippable by fingers so that it can be held irrotationally in place while coupler nut is tightened or loosened.

Figure 11:
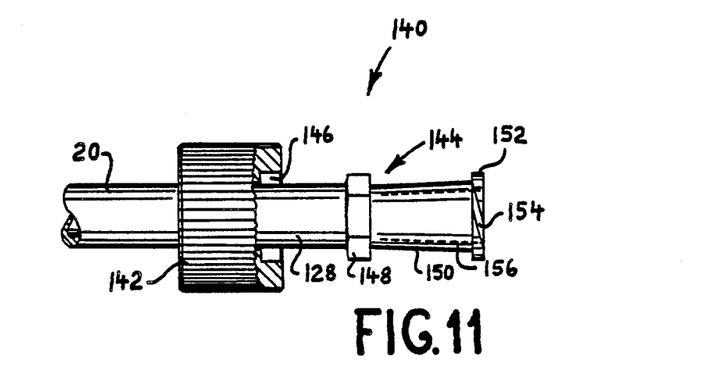
FIG. 11 is a schematic side view and partial section of an embodiment of an intermediate coupling adaptor for connecting bridge means (included in the depictions of FIGS. 1 and 9) to an endoscope, the adaptor being shown attached to a passage entry housing of an endoscope.

Referring now to FIG. 11, connected to passage entry housing 20 is shown a coupler adaptation means 140, comprising a coupler nut 142, a coupler tube 144, and the here not visible collar means 122 (FIG. 10). Coupler adaptation means 140 is in many respects similar to coupler adaptation means 117 (FIG. 10). In particular, the structure hidden by the not sectioned portion of coupler nut 142 is identical to the structure disposed within coupler nut 120 of FIG. 10. Coupler nut 142 additionally is provided with a cavity 146 disposed adjacently and open to its right hand face. Cavity 146 is preferably hexagonal. Coupler tube 144, aside from comprising the here not visible tapered end 124 and ridge 126, and the partly visible shank portion 128, further comprises a shoulder 148 and a female cone adaptor 150, the latter being preferably of a "Luer" lock adaptor type. Shoulder 148 is preferably of a shape to be able to irrotationally engage cavity 146; for instance, a hexagonal shape as shown here. The latter facility is provided to serve ease of disconnection by facilitating a twisting motion of unscrewed coupler nut 142 and therewith of coupler tube 144 while tapered end 124 (wedged in passage entry housing 20) is withdrawn.

Female cone adaptor 150 includes a collar 152 that is provided with thread-engaging means 154 for engaging matching screw thread nuts of further connectors, that are preferably also of a "Luer" lock type. Female cone adaptor 150 includes a tapered bore 156 to sealedly engage appropriately shaped male tube members of other connectors inserted therein; for example male "Luer" type connectors. Coupler adaptation means 140 is provided to serve for connecting securely and sealedly between passage entry housings 20 of endoscopes not equipped with "Luer" lock type entries, as hereinbefore described, and proximal catheter-encircling ends of expandable catheter and bridge devices of the present invention, wherein the proximal catheter-encircling end 26 is adapted with a "Luer" lock type connector, for instance as shown in FIG. 3 (attachment means 62, conical taper 66, screw threads 68). It will be recognized that coupler adaptation means 140 can also serve advantageously for coupling adaptation between any device having a passage entry as described for passage entry housing 20 in FIGS. 10 and 11, and any male "Luer" type connector.

Other coupling attachment or adaptation means than the shown embodiments of FIGS. 10 and 11 (coupler adaptation means 117 and 140, respectively) can be used alternatively. For instance, internal screw threads of coupler nuts 120 or 142 can be replaced by an appropriately located internal groove (or ridge) so that secure attachment to ridge 126 is provided by snap-action when the nut is forced axially over ridge 126. Appropriate interfering diameters and elastic deformation of such nuts provide for adequate securing of the parts.

Referring back to FIGS. 1 and 9, typical dimensions for bridge means 24 are as follows: The distance between proximal and distal catheter-encircling ends is in the range of about three to four inches, and preferably about three and one half inches; the distance between the approximate middle of the bow-section of bridge means 24 and catheter means 32 is in the range of about three quarters to one and a half inches, and preferably about one inch. Additionally referring back also to FIG. 2, typical dimensions for catheter means 32 are as follows: The length of inextensible section 34 is between about four and seven inches, and preferably about five and one half inches. Prior to having been expanded, the length of expandable section 36 is in the range of about nine to twelve inches, and preferably about ten and one half inches; subsequent to having been expanded, the length of expandable section 36 is in the range of about eighteen to twenty four inches, and preferably about twenty one inches. Expandable section 36 is preferably expandable to about twice its unexpanded length. It should be noted in this respect that the given catheter length dimensions relate to catheter means 32 for use in adult patients. Correspondingly shorter lengths are appropriate for pediatric procedures, and different lengths can be provided to suit veterinary procedures.

The expandable catheter and bridge device of the invention is advantageously prepackaged after manufacture in a sterilized manner so that it is ready for use upon unpacking without a need for sterilization. Additionally, it has been found that inextensible (conventional) catheters, necessarily having rather long lengths, and that are therefore sometimes packaged in multiply bent or rolled shapes, acquire a certain degree of set due to this packaged form. Such sets can disadvantageously influence manipulation during deployment. The significantly shorter lengths of catheter means 32 of the present invention permit easy packaging in the preferred linear and unstrained form, and thusly avoid such disadvantages or difficulties.

A prepackaged expandable catheter and bridge device can preferably include also coupler adaptation means, such as coupler adaptation means 140 (FIG. 11) to provide a ready adaptation capability to a variety of conventional endoscope passage entry housings (as hereinbefore described).

It will be realized in view of the given presentations that other than the described connecting adaptors can be alternatively used, for instance to connect proximal catheter-encircling end 26 to passage entry housing 20 of an endoscope and to connect further instruments (as syringes) to distal end of catheter means 32. A variety of standardized customarily available connectors and adaptors in different sizes are available for surgical instrumentation purposes including uses in catheterization and urological procedures. Since "Luer" lock type connectors and adaptors are among the most commonly used ones, this type is preferred for use in the device of the invention, although other types may be equally as suitable.

In view of the relatively low cost of the expandable catheter and bridge device of the invention, one-time use and disposability thereof is preferred.

In accordance with the invention, the expandable catheter means 32 as herein described can be advantageously used without employment of bridge means 24 in catheterization procedures by virtue of its longitudinal expansion capability. The expansion capability provides for a wide range of usable lengths being available from one stock length and clearly reduces the need for stocking of numerous different lengths for different applications and procedural situations. Just prior to use, catheter means 32 is either manually pre-expanded to a desired length, or it is expanded, as needed, during use by appropriate manual tensioning. This device has also the added advantage in that it ca be pre-packaged in smaller and shorter packages (and in linearly layed out, unstressed form) than is feasible for conventional inextensible catheters.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. An expandable catheter and bridge device for use in combination with endoscopic instruments in catheterization procedures, comprising:
    catheter means including
        a catheter tube for catheterization use, said catheter tube having a proximal and a distal end,
        a longitudinally inextensible section proximate said proximal end,
        a longitudinally expandable section proximate said distal end, said inextensible and expandable sections forming a continuous catheter conduit between said proximal and distal ends, said continuous catheter conduit being laterally flexible; and
    bridge means of substantially rigid structure for supporting and guiding said catheter tube, and for expanding said longitudinally expandable section, said bridge means including
        a bowed section having a proximal catheter-encircling end at one end thereof and a distal catheter-encircling end at another end thereof for guiding said catheter means therethrough, said bowed section having a generally bow-like shape to facilitate manipulation of said catheter tube while said catheter tube is disposed between said proximal catheter-encircling end and said distal catheter-encircling end.

2. The device according to claim 1, wherein said proximal catheter-encircling end comprises attachment means for sealedly securing said proximal catheter-encircling end to a passage entry of said endoscopic instruments.

3. The device of claim 2, wherein said attachment means comprises a coupler nut and a collar means having external screw threads thereon, said passage entry being formed in a tubular passage housing having an outside diameter and a larger-diameter lip disposed about the periphery thereof at an entry face of said tubular passage housing,
    said collar means having a radial split and comprising hinge means so that said collar means can be hinged open for mounting around said outside diameter of said tubular passage housing adjacent to said lip and so that said collar means can be hinged closed thereafter to substantially encircle said outside diameter, said coupler nut being retained along said proximal catheter-encircling end, said coupler nut having internal screw threads that engage said external screw threads on said collar means to couple said proximal catheter-encircling end to said passage entry.

4. The device of claim 2, wherein said attachment means comprises a Luer lock connection for attachment to a mating Luer lock adaptor disposed at said passage entry of said endoscopic instruments.

5. The device according to claim 1 further comprising coupler adaptation means having a Luer lock connection for coupling said proximal catheter-encircling end to an endoscopic instrument.

6. The device according to claim 1, wherein said distal catheter-encircling end comprises expanding means for expanding said longitudinally expandable section while said longitudinally expandable section is axially drawn therethrough.

7. The device according to claim 1, wherein said catheter means is threaded through said distal and proximal catheter-encircling ends so that said proximal end extends beyond said proximal catheter-encircling end for insertion into a passage entry of said endoscopic instruments and said distal end extends beyond said distal catheter-encircling end.

8. The device according to claim 1, wherein said proximal end is provided with a tip so shaped as to facilitate entry into urethral and ureteral passages, said tip including at least one external opening in communication with the bore of said catheter tube for passing fluids therethrough.

9. The device according to claim 1, wherein said distal end is provided with a connection adaptor including a flexible captively-attached closure cap,
    said connection adaptor serving for secure selective connection of said distal end to further instrument means to provide communication between the bore of said catheter tube and said further instrument means,
    said flexible captively-attached closure cap serving for optionally securely capping said connection adaptor and thereby blocking the bore of said catheter tube to prevent communication thereof at said distal end with ambient conditions.

10. The device of claim 9, wherein said connection adaptor is a female Luer lock connection adaptor, and wherein said flexible captively attached closure cap is a male Luer lock cap.

11. The device according to claim 1, wherein said longitudinally expandable section comprises a corrugated tubular wall to provide for a longitudinal expandability thereof so that said longitudinal expandable section can be stretched in length and remain thusly stretched while retaining substantial resistance against being longitudinally compressed thereafter.

12. The device of claim 11, wherein the ratio of the expanded length of said expandable section to the unexpanded length thereof is about two to one.

13. The device according to claim 1, wherein said bridge means further comprises a cradle disposed upon said bowed section for selective retention of a syringe.

14. The device according to claim 1, wherein said distal catheter-encircling end comprises expanding means for expanding said longitudinally expandable section of said catheter means while said longitudinally expandable section is axially drawn therethrough, said expanding means comprising a bore tapered down in direction toward said proximal catheter-encircling end, said bore having an entry diameter and an exit diameter, said entry diameter being at least as large as the outside diameter of said longitudinally expandable section prior to having been expanded, said exit diameter being no larger than the relaxed outside diameter of said longitudinally expandable section subsequent to having been expanded; and, said bore having substantially smoothly tapering walls between said entry and exit diameters.

15. The device according to claim 1, wherein said distal catheter-encircling end comprises expanding means for expanding said longitudinally expandable section of said catheter means while said longitudinally expandable section is axially drawn therethrough, said expanding means comprising a bore having a smallest diameter at least as large as the outside diameter of said longitudinally expandable section in expanded form;
   said bore having a face ledge facing distally, said face ledge having an outer diametral extent that is at least as large as the unexpanded outside diameter of said longitudinally expandable section.

16. The device according to claim 1, wherein said distal catheter-encircling end is comprised of split portions that are alignedly joined to one another subsequent to insertion of said catheter means therebetween.

17. The device of claim 16, wherein said split portions are joined to one another by ultrasonic welding.

18. The device of claim 16, wherein said split portions are joined to one another by snap-fit fastening means.

19. The device according to claim 1, wherein said proximal catheter-encircling includes means defining a guide hole for guiding said catheter means therethrough, said guide hole having a diameter at least as large as the outside diameter of said longitudinally expandable section subsequent to having been expanded; and, said longitudinally inextensible section having an outside diameter about equal to the outside diameter of said longitudinally expandable section subsequent to expansion thereof.

20. The device according to claim 1, wherein said proximal catheter-encircling end comprises sealing means for sealing thereto outside diameters of said longitudinally inextensible section and of said longitudinally expandable section when the latter is in expanded form.

21. The device of claim 20, wherein said sealing means is adjustable to provide adjustability of slidable sealing, said sealing means being further selectively adjustable to substantially immovably sealably clamp said catheter means in selected axial positions thereof.

22. The device according to claim 1, wherein said proximal and distal catheter-encircling ends each include an opening therethrough, said openings being substantially aligned along a common axis.

23. The device according to claim 1, wherein said catheter means and said bridge means are comprised of sterilizable plastic materials.

24. The device of claim 1, wherein said catheter means is in a generally linear and unstrained shape.

25. The device according to claim 1, wherein the distance between said proximal and distal catheter-encircling ends is between about three and four inches, and wherein the distance between about the middle of said bowed section and said catheter tube is between about three quarters and one and one-half inches.

26. The device according to claim 1, wherein the length of said longitudinally inextensible section is between about four and seven inches, and wherein the length of said longitudinally expandable section, prior to having been expanded, is between about nine and twelve inches.

27. The device of claim 26, wherein the expanded length of said longitudinally expandable section is between about eighteen and twenty four inches.

28. An expandable catheter and bridge device for use in combination with endoscopic instruments in urological catheterization procedures, comprising:
   catheter means including
      a catheter tube for catheterization use, said catheter tube having a proximal and a distal end,
      a longitudinally inextensible section proximate said proximal end,
      a longitudinally expandable section proximate said distal end, said inextensible and expandable sections forming a continuous catheter conduit between said proximal and distal ends, said continuous catheter conduit being laterally flexible;
   bridge means of substantially rigid structure for supporting and guiding said catheter tube, and for expanding said longitudinally expandable section, said bridge means including
   a bowed section having a proximal catheter-encircling end at one end thereof and a distal catheter-encircling end at the other end thereof for guiding said catheter means therethrough, said bowed section having a generally bow-like shape to facilitate manipulation of said catheter tube while said catheter tube is disposed between said proximal catheter-encircling end and said distal catheter-encircling end;
   attachment means included in said proximal catheter-encircling end for securing said proximal catheter-encircling end to said endoscopic instruments; and
   expanding means included in said distal catheter-encircling end for expanding said longitudinally expandable section when said longitudinally expandable section is axially drawn therethrough; said catheter means being threaded through said distal and proximal catheter-encircling ends and having said proximal end extend beyond said proximal catheter-encircling end for insertion into said endoscopic instrument and having said distal end extend beyond said distal catheter-encircling end.

29. The device according to claim 28, wherein said endoscopic instrument includes a passage entry formed in a tubular housing, said passage entry having an outside diameter and a larger diameter lip disposed about the periphery thereof at an entry face of said tubular passage housing, said device further including:
   attachment means including a coupler nut and collar means, said collar means having a radial split and comprising hinge means so that said collar means can be hinged open for mounting around said outside diameter of said tubular housing adjacent to said lip and so that said collar means can be hingedly closed to substantially encircle said outside diameter;
   said coupler nut being retained along said proximal catheter-encircling end, and having internal screw threads that engage external screw threads on said collar means to couple said proximal catheter-encircling end to said passage entry.

30. An expandable catheter device for use in catheterization procedures, comprising:
   catheter means including
      a catheter tube for catheterization use, said catheter tube having a proximal and a distal end,
      a longitudinally inextensible section proximate said proximal end,
      a longitudinally expandable section proximate said distal end, said inextensible and expandable sections forming a continuous catheter conduit, said continuous catheter conduit being laterally flexible;

said catheter tube being introduced by said proximal end into bodily passages during said catheterization procedures, said longitudinally expandable section being added for selective expansion prior to introduction thereof into said bodily passages so that its length is in accord with the particular catheterization procedure to be performed; and said expandable catheter device further including bridge means for connection to a passage entry of an endoscopic instrument, said bridge means including a bowed section and proximal and distal catheter-encircling ends, said proximal catheter-encircling end being securely connectable to said passage entry;

said distal catheter-encircling end comprising expanding means for expanding said longitudinally expandable section, said longitudinally expandable section being adapted to be expanded in said expanding means while being drawn therethrough.

31. Coupler adaptation means for coupling adaptation between first and second tubular passage members of surgical instruments of the type in which said first tubular portion has an entry face, said coupler adaptation comprising:

means within said first tubular passage member including a passageway having an outside diameter and a larger diameter lip disposed about the periphery thereof at said entry face of said first tubular passage member, and wherein said second tubular passage member comprises a Luer lock connector, said coupler adaptation means further comprising:

a coupler tube including at a first end thereof a matching connector to mate with said Luer lock connector;

a coupler nut; and collar means; said collar means having a radial split and comprising hinge means so that said collar means can be hinged open for mounting around said outside diameter of said first tubular passage member adjacent to said lip and so that said collar means can be hinged closed to substantially encircle said outside diameter;

said coupler nut being retained along said coupler tube;

said coupler nut having internal screw threads that engage external screw threads on said collar means to couple said first tubular passage member to said coupler tube.

32. A bridge means for supporting and guiding a catheter tube of the type that is inserted into a passage entry of an endoscopic instrument, said catheter tube having a proximal and a distal end, said bridge means comprising:

a bowed section having proximal and distal ends and an intermediate portion;

a proximal catheter-encircling means located at said proximal end and a distal catheter-encircling means located at said distal end;

said bridge means being thereby adapted to accommodate a catheter tube to be threaded through said proximal and distal catheter-encircling means for disposition therebetween for manipulation of said catheter tube during such disposition;

said proximal catheter-encircling means including attachment means for sealedly securing said proximal catheter-encircling means to said passage entry of said endoscopic instrument;

said distal catheter-encircling means including expanding means for expanding said catheter tube longitudinally while said catheter tube is threaded therethrough and while said catheter tube is being manipulated during insertion into said passage entry, said catheter tube being longitudinally expandable over at least a portion of the length thereof.

33. The bridge means of claim 32 wherein said attachment means comprises a coupler nut and a collar means having external screw threads thereon, said passage entry being formed in a tubular passage housing having an outside diameter and a larger-diameter lip disposed about the periphery thereof at an entry face of said tubular passage housing, said collar means having a radial split and comprising hinge means so that said collar means can be hinged open for mounting around said outside diameter of said tubular passage housing adjacent to said lip and so that said collar means can be hinged closed thereafter to substantially encircle said outside diameter, said coupler nut being retained along said proximal catheter-encircling end, said coupler nut having internal screw threads that engage said external screw threads on said collar means to couple said proximal catheter-encircling end to said passage entry.

34. The bridge means of claim 32 wherein said attachment means comprises a Luer lock connection for attachment to a mating Luer lock adaptor disposed at said passage entry of said endoscopic instruments.

35. The bridge means of claim 32 further including a cradle disposed on said bowed section for optional retention of a manually operatable syringe while said manually operatable syringe is coupled to said distal end of said catheter tube.

36. The bridge means of claim 32 wherein said distal catheter-encircling means includes split portions that are alignedly joined to one another subsequent to insertion of said catheter tube therebetween.

37. The bridge means of claim 32 wherein said endoscopic instrument includes a passage entry formed in a tubular housing, said passage entry having an outside diameter and a larger diameter disposed about the periphery thereof at an entry face of said tubular passage housing, said bridge means further including in said attachment means:

a coupler nut and collar means, said collar means having a radial split and comprising hinge means so that said collar means can be hinged open for mounting around said outside diameter of said tubular housing adjacent to said lip and so that said collar means can be hingedly closed to substantially encircle said outside diameter;

said coupler nut being retained along said proximal catheter-encircling means, and having internal screw threads that engage external screw threads on said collar means to couple said proximal catheter-encircling means to said passage entry.

* * * * *